US006358713B1

(12) United States Patent
Green

(10) Patent No.: US 6,358,713 B1
(45) Date of Patent: Mar. 19, 2002

(54) IN VITRO RIBOSOME EVOLUTION

(75) Inventor: Rachel Green, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/547,537

(22) Filed: Apr. 12, 2000

Related U.S. Application Data
(60) Provisional application No. 60/128,848, filed on Apr. 12, 1999.

(51) Int. Cl.⁷ ................................................. C12Q 1/68
(52) U.S. Cl. .......................................... 435/91.1; 435/6
(58) Field of Search ....................... 435/6, 91.1; 514/44

(56) References Cited

U.S. PATENT DOCUMENTS

| | | | | |
|---|---|---|---|---|
| 4,743,535 A | * | 5/1988 | Carrico | ........................... 435/6 |
| 5,643,722 A | | 7/1997 | Rothschild et al. | |
| 5,872,104 A | | 2/1999 | Vermeulen et al. | ............ 514/29 |
| 5,962,244 A | * | 10/1999 | Lynch et al. | ................... 435/15 |
| 5,965,695 A | | 10/1999 | Simon et al. | ................ 530/324 |

FOREIGN PATENT DOCUMENTS

| | | |
|---|---|---|
| WO | WO 98/31700 | 7/1998 |
| WO | WO 00/09737 | 2/2000 |

OTHER PUBLICATIONS

Lohse et al.,"Ribozyme–catalysed amino–acid transfer reactions"; Nature 1996, vol. 381, pp. 442–444.*
Schumacher et al., "Identification of D–Peptide Ligands Through Mirror–Image Phage Display", 1996, vol. 271, pp. 1854–1857.*
Steiner et al.,"Photo–affinity labelling at the peptidyl transferase center reveals two different positions for the A– and P–sites in domain V of 23S rRNA";The EMBO Journal, 1988, vol. 7, No. 12, pp. 3949–3955.*
Green et al., "Localization of The A Site On The Ribosome"; The Second Annual Meeting of the RNA Society, 1997, May 27–Jun. 1, Banff Centre, Banff, Alberta.*
Kuyl–Yeheskiely,"An expeditious route to methylphosphonate analogues of DNA", Recl. Trav. Chim. Pays–Bas, 1993, 113, pp. 040–044.*
Green, et al., RNA '97, 1997, p. 87.
Green, et al., Science, 1998, 280:286–289.
Lohse and Szostak, Nature, 1996, 381:442–444.
Cadwell, R., et al., "Randomization of Genes by PCR Mutagenesis," PCR Methods and Applications, (1992) vol. 2, No. 1, pp. 28–33.
Green, R., et al., "Reconstitution of Functional 50S Ribosomes from in Vitro Transcripts of *Bacillus stearothermophilus* 23S rRNA," Biochemistry (1999) vol. 38, No. 6, pp. 1772–1779.
Kuechler, E., et al., "Aromatic Ketone Derivatives of Aminoacyl–tRNA as Photoaffinity Labels for Ribosomes," Methods in Enzymology (1977) vol. 46, pp. 676–683.

Lorsch, J., et al., "In vitro evolution of new ribozymes with polynucleotide kinase activity,", Nature (1994) vol. 371, No. 6492, pp. 31–36.

Green, R., et al., "In vitro genetic analysis of the Tetrahymena self–splicing intron," Nature (1990) vol. 347, No. 6290, pp. 406–408.

Roberts, R., et al., "RNA–peptide fusions for the in vitro selection of peptides and proteins," *Proc. Natl. Acad. Sci, USA* (*1997*) vol. 94, pp. 12297–12302.

Atkinson, T., et al., "Solid–phase Synthesis of Oligodeoxyribonucleotides by the Phosphite–triester Method," Oligonucleotide Synthesis: a practical approach, Oxford: IRL Press (1985) pp. 35–81.

Green, R.,et al., "In vitro complementation analysis localizes 23S rRNA posttranscriptional modifications that are required for *Escherichia coli* 50S ribosomal subunit assembly and function," RNA (1966) vol. 2, No. 10, pp. 1011–1021.

Powers, T., et al., "A functional pseudoknot in 16S ribosomal RNA," The EMBO J. (1991) vol. 10, No. 8, pp. 2203–2214.

Breitmeyer, J., et al., "Affinity Labeling of Specific Regions of 23 S RNA by Reaction of N–bromoacetyl–phenylalanyl––transfer RNA with *Escherichia coli* Ribosomes," J. Mol. Biol. (1976) vol. 101, pp. 297–306.

Milligan, J., et al., "Oligoribonucleotide synthesis using T7 RNA polymerase and synthetic DNA templates," Nucleic Acids Research (1987) vol. 15, No. 21, pp. 8783–8798.

Powers, T., et al., "Dominant lethal mutations in a conserved loop in 16S rRNA," Proc. Natl. Acad. Sci. USA (1990) vol. 87, pp. 1042–1046.

Porse, B., et al., "Mapping Important Nucleotides in the Peptidyl Transferase Centre of 23 S rRNA using a Random Mutagenesis Approach," J. Mol. Biol. (1995) vol. 249, No. 1, pp. 1–10.

Noller, H., et al., "Unusual Resistance of Peptidyl Transferase to Protein Extraction Procedures," Science (1992) vol. 256, pp. 1416–1419.

Samaha, R., et al., "A base pair between tRNA and 23S rRNA in the peptidyl transferase centre of the ribosome," Nature (1995) vol. 377, pp. 309–314.

Green, R., et al., "Ribosomes and Translation," Annu. Rev. Biochem (1997) vol. 66, pp. 679–716.

(List continued on next page.)

*Primary Examiner*—Eggerton A. Campbell
(74) *Attorney, Agent, or Firm*—Fish & Richardson, P.C.

(57) ABSTRACT

Methods for selecting rRNA variants that catalyze formation of non-standard polymers are described.

19 Claims, 5 Drawing Sheets

OTHER PUBLICATIONS

Moazed, D., et al., "Interaction of tRNA with 23S rRNA in the Ribosomal A, P, and E sites," Cell (1989) vol. 57, No. 4, pp. 585–597.

Kim, D., et al., "Base–Pairing between 23S rRNA and tRNA in the Ribosomal A Site," Molecular Cell (1999) vol. 4, No. 5, pp. 859–864.

Steiner, G., et al., "Photo–affinity labeling at the peptidyl transferase centre reveals two different positions for the A– and P–sites in domain V of 23S rRNA," The EMBO Journal (1988) vol. 7, No. 12, pp. 3949–3955.

Simon, R., et al., "Peptoids: A modular approach to drug discovery," Proc. Natl. Acad. Sci. USA (1992) vol. 89, pp. 9367–9371.

Ellman, J., et al., "Site–Specific Incorporation of Novel Backbone Structures into Proteins," Science (1992) vol. 255, pp. 197–200.

Tarussova, N. B., et al., "Synthesis of an Unnatural P–N Bond Catalyzed With *Escherichia Coli* Ribosomes," FEBS Lett. (1981) vol. 130, No. 1, pp. 85–87.

Schumacher, T., et al., "Identification of D–Peptide Ligands Through Mirror–Image Phage Display," Science (1996) vol. 271, pp. 1854–1857.

Brosius, J., et al., "Complete nucleotide sequence of a 23S ribosomal RNA gene from *Escherichia coli*," Proc. Natl. Acad. Sci. USA (1980) vol. 77, No. 1, pp. 201–104.

Kop, J., et al., "Complete Nucleotide Sequence of a 23S Ribosomal RNA Gene from *Bacillus stearothermophilus*," DNA (1984) vol. 3, No. 5, pp. 347–357.

Ajuh, P., et al., "*Xenopus borealis* and *Xenopus laevis* 28S ribosomal DNA and the complete 40S ribosomal precursor RNA coding units of both species," Proc. R. Soc. Lond. B (1991) vol. 245, pp. 65–71.

Hassouna, N., et al., "The complete nucleotide sequence of mouse 28S rRNA gene. Implications for the process of size increase of the large subunit rRNA in higher eukaryotes," Nucleic Acids Research (1984) vol. 12, No. 8, pp. 3563–3583.

Urlaub, H., et al., "Protein–rRNA binding features and their structural and functional implications in ribosomes as determined by cross–linking studies," The EMBO Journal (1995) vol. 14, No. 18, pp. 4578–4588.

* cited by examiner

IN VITRO RIBOSOME EVOLUTION

CROSS-REFERENCE TO RELATED APPLICATIONS

This application claims priority from U.S. Provisional Application No. 60/128,848, filed Apr. 12, 1999.

STATEMENT AS TO FEDERALLY SPONSORED RESEARCH

Funding for the work described herein was provided in part by the federal government, which has certain rights in the invention.

TECHNICAL FIELD

The invention relates to selection of variant rRNA molecules catalyzing formation of non-peptidyl products when incorporated into large ribosomal subunits.

BACKGROUND

Catalysis of peptide bond formation requires precise juxtaposition by the ribosome of the acceptor ends of P (peptidyl) and A (aminoacyl) site bound tRNAs in its "active site". Accumulating evidence points to a functionally important role for rRNAs in the various steps of the translational cycle, and in particular in peptidyl transferase. See, for example, Noller et al., *Science,* 1992, 256:1416–1419; and Samaha et al., *Nature,* 1995, 377:309–314. A number of approaches have begun to identify specific nucleotides in 23S rRNA that are located proximal to the tRNA substrates of the ribosome. See review by Green and Noller, *Ann. Rev. Biochem.,* 1997, 66:679–716. Studies by Moazed and Noller identified a small number of nucleotides in domain V of 23S rRNA whose protection from chemical modification is dependent on the presence of the CCA acceptor ends of A and P-site bound tRNAs. Moazed and Noller, *Cell,* 1989, 57:585–597. While these critical nucleotides are predominantly found in the central loop structure of domain V, several are located in peripheral elements of this 23S RNA domain including the 2250 and the 2555 loops. Discovery of a base-pairing interaction between C74 of P-site-bound tRNA and G2252 of domain V established a direct functional role for this region of 23S rRNA in peptidyl transferase (PT). Samaha et al., 1995, supra. Recent experiments describing an interaction between C75 of A site tRNA and G2553 of 23S rRNA further substantiate this role. Kim and Green, *Mol. Cell,* 1999, 4:859–864. Characterization of a P-site-specific peptidyl transferase-reactive crosslink between a benzophenone derivatized peptidyl-tRNA and A2451/C2452 in the central loop of domain V of 23S rRNA identified this region as another likely component of the active site of 23S rRNA. Steiner et al., *EMBO J.,* 1988, 7:3949–3955.

SUMMARY

The invention is based on a method for evolving or redirecting the standard peptidyl transferase chemistry that is performed by the ribosome. Specifically, an iterative, in vitro selection system is described that allows for the isolation of variant major rRNAs of large ribosomal subunits with novel properties. The selection system allows rRNA variants to be isolated with enriched catalytic activity on altered peptidyl and aminoacyl ribosome substrates such as D-amino acids, methyl phosphinyl derivatized substrates, N-derivatized, and β-amino acid substrates. The coupling of such evolved ribosomes with RNA-peptide fusion technology allows for the generation of combinatorial chemical libraries that can be screened and deconvoluted to identify novel and biologically stable target compounds.

The invention features a method for selecting rRNA variant molecules catalyzing formation of non-peptidyl products. The method includes crosslinking a peptidyl substrate to ribosomes, wherein the major RNA of the large ribosomal subunit in a plurality of the ribosomes is an rRNA variant molecule. The ribosomes can be eukaryotic or prokaryotic ribosomes, such as *Escherichia coli* or *Bacillus stearothermophilus* ribosomes, and the rRNA variant can be a 28S or 23S rRNA variant molecule.

The crosslinked ribosomes and a labeled, derivatized aminoacyl substrate are reacted under conditions such that the labeled, derivatized aminoacyl substrate is transferred to the rRNA variant molecule to form labeled ribosomes. The rRNA variant molecules are selected from labeled ribosomes. The peptidyl substrate can be a benzophenone derivatized peptidyl substrate, and the labeled, derivatized aminoacyl substrate can be N-derivatized, a β-amino acid, or a D-amino acid. The labeled, derivatized aminoacyl substrate can be biotinylated or can include a thiol moiety. The method further can include repeating the method steps with the selected rRNA variant molecules.

The invention also features a method for selecting rRNA variant molecules catalyzing formation of non-peptidyl products that includes crosslinking an aminoacyl substrate to ribosomes, wherein the major RNA of the large ribosomal subunit in a plurality of the ribosomes is an rRNA variant molecule. The rRNA variant molecule is thr major RNA of the large ribosomal subunit as described above. The crosslinked ribosomes and a labeled, derivatized peptidyl substrate are reacted under conditions such that the labeled, derivatized peptidyl substrate is transferred to the rRNA variant molecule to form labeled ribosomes. The labeled rRNA variant molecules are selected from the labeled ribosomes. The aminoacyl substrate can be 4-thio-dT-p-C-p-Puromycin, and the labeled, derivatized peptidyl substrate can include a methyl phosphinyl derivatized peptidyl substrate or a D-amino acid. The method further can include repeating the method steps with the selected rRNA variant molecules.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
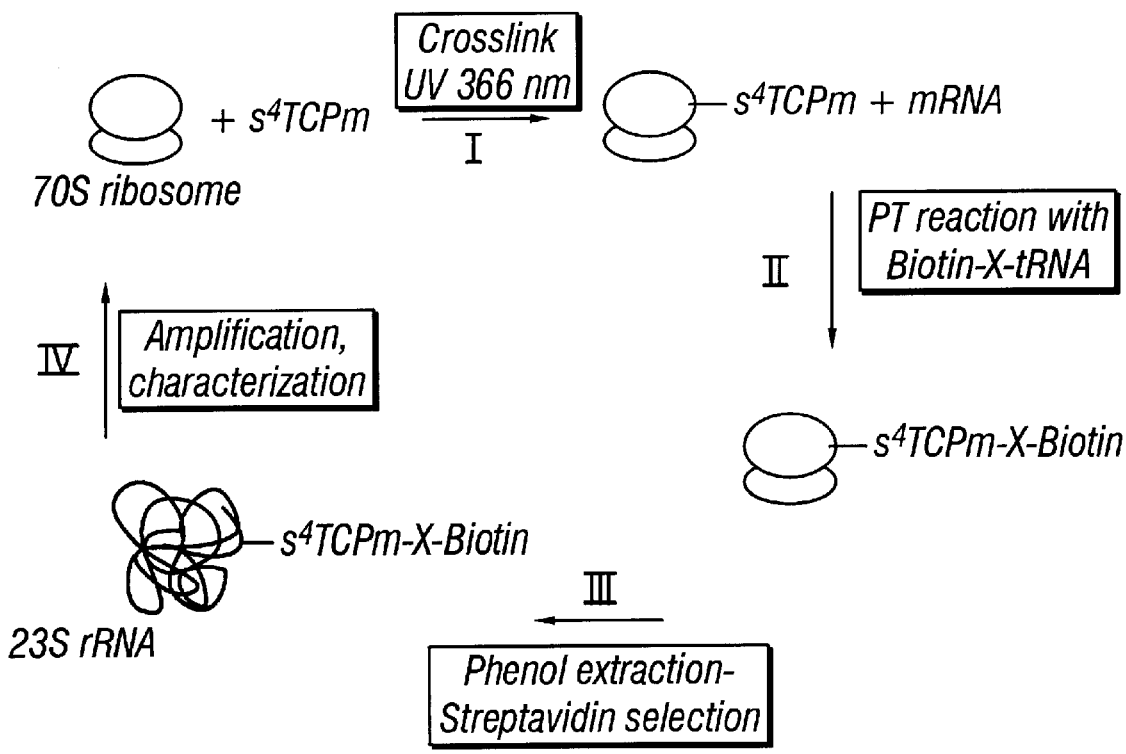
FIG. 1 is a schematic that depicts use of an aminoacyl crosslinking agent in the general steps for selecting variant rRNAs.

The ribosome is the biological machine that takes the genetic information in the cell found in the DNA and translates it into the more generally functional protein molecules. Proteins (or peptides) are polymers composed of twenty different amino acids strung linearly together via peptide bonds. These molecules form complicated three-dimensional structures able to perform most cellular functions. These molecules, however, have limited lifetimes in the confines of the cell due to the existence of proteolytic machinery that specifically cleaves peptide bonds. Thus, in spite of their diversity in structure and function, the therapeutic value of peptide-based drugs is limited by their in vivo lifetime.

As described herein, the in vitro selection system provides rRNA variants that efficiently transform ribosomes into machines that generate encoded polymers composed of non-standard backbones (i.e. non-peptide) or polymers in a non-standard configuration (D-configuration). The properties of a number of alternative polymers have been studied, for example, polymers including N-derivatized amino acids (i.e., peptoids), D-amino acids, and β-amino acids. See, for example, Simon et al., *Proc. Natl. Acad. Sci. USA*, 1992, 89:9367–9371; Ellman et al., *Science*, 1992, 255:197–200; Tarussova et al., *FEBS Lett.*, 1981, 130(1):85–87; Schumacher et al., *Science*, 1996 271:1854–7, and U.S. Pat. No. 5,965,695. Other alternative polymers, such as phosphonate derivatives, already have demonstrated therapeutic application as protease inhibitors against HIV. Encoded libraries of such compounds can be screened for drug candidates having novel biological properties and increased stability in the cell.

Overview of Selection Methods

In general, the selection is performed by crosslinking a substrate to a population of ribosomes, wherein each ribosome contains a different variant rRNA, subsequently reacting the crosslinked ribosomes with a labeled, derivatized substrate, and selecting labeled ribosomes. As used herein, "label" refers to a moiety that does not interfere with the catalytic activity of the ribosome and that can be detected, either directly or indirectly. Non-limiting examples of labels include radioisotopes, biotin, or thiol derivatization. As used herein, "derivatized substrates" refer to aminoacyl or peptidyl substrates that form non-standard polymers. Such polymers can include polymers with a non-peptide backbone or bond, i.e., a non-amide bond, or polymers in the D-configuration rather than the L-configuration. Non-limiting examples of derivatized substrates include methylphosphinyl substrates, D-amino acid substrates, N-derivatized substrates, or β-amino acids. Substitution of a methylphosphinyl moiety for the aminoacyl ester bond in the donor substrate of the ribosome results in a phosphinoamide bond. Phosphinoamide bonds generally are more biologically stable than peptide bonds, and have a tetrahedral geometry. D-amino acids form D-peptides that are resistant to cellular processes. Substitution of a N-derivatized substrate such as N-substituted glycine results in the generation of peptoids, whereas substitution of β-amino acids results in a peptide-like backbone having an extra methylene group. Competent ribosomes, i.e., ribosomes able to catalyze formation of non-standard polymers, are distinguished from non-competent ribosomes by the presence of the label on the major rRNA.

Figure 2:
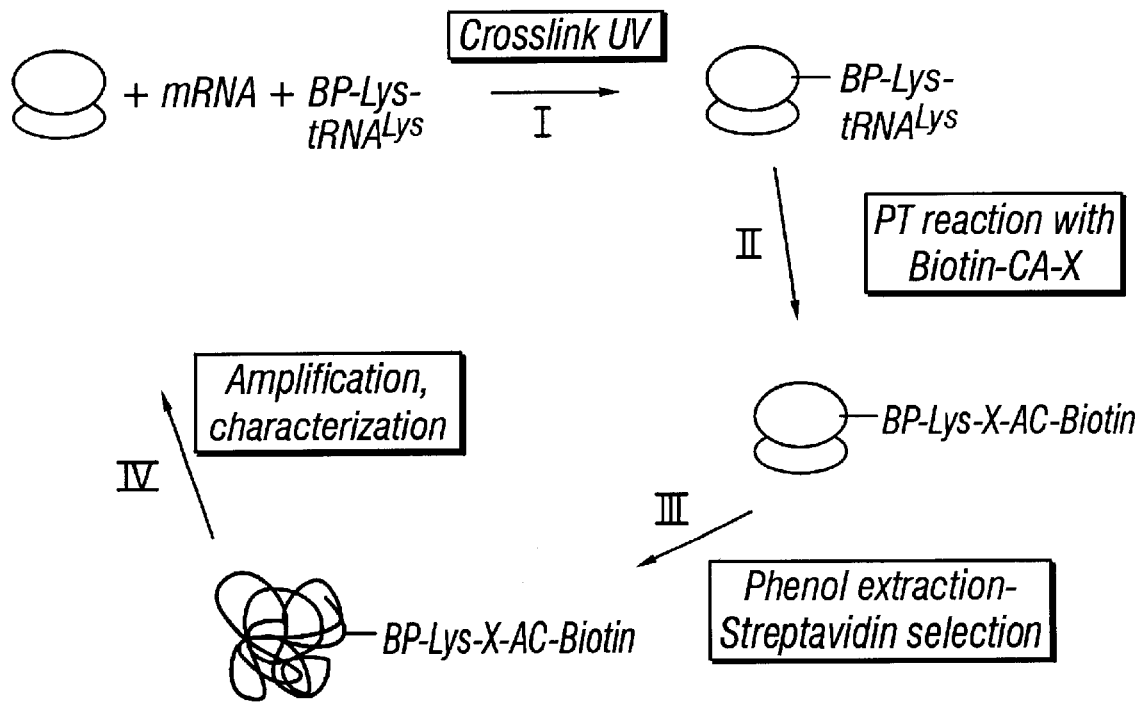
FIG. 2 is a schematic that depicts use of a peptidyl crosslinking agent in the general steps for selecting variant rRNAs.

More specifically, the selection can be performed by crosslinking an aminoacyl substrate to the ribosome and reacting with a labeled, derivatized peptidyl substrate, or by crosslinking a peptidyl substrate to the ribosome and reacting with a labeled, derivatized aminoacyl substrate, such that a non-standard polymer is formed. FIGS. 1 and 2 are schematics that provide an example of each selection procedure. For example, the aminoacyl substrate 4-thio-dT-p-C-p-Puromycin (s$^4$TCPm), which crosslinks with high efficiency and specificity to the 23S rRNA, and which remains fully active in a subsequent peptidyl transferase reaction, can be covalently linked to ribosomes that contain a variant rRNA in the active site of the ribosome. The tethered substrate then is reacted in a ribosomal reaction with a labeled, derivatized peptidyl substrate such as a labeled, methylphosphinyl peptidyl substrate. After accepting the growing polymer, puromycin falls off the ribosome, terminating elongation of the polymer. Alternatively, a peptidyl substrate can be crosslinked to the ribosome, and reacted with a labeled, derivatized aminoacyl substrate. For example, a benzophenone derivatized peptidyl substrate can be covalently linked to the variant rRNA, and the ribosomes containing the variant rRNA then can be reacted with a labeled, derivatized aminoacyl substrate, such as a labeled, N-derivatized aminoacyl substrate.

After such reactions, catalytically competent ribosomes can be physically isolated from the non-competent population as the ribosomes now carry a label. The selected rRNA population then, for example, can be amplified by reverse transcription and polymerase chain reaction (PCR), to provide an enriched population of RNAs that can be retranscribed for iterative processing through the selection cycle.

Variant rRNAs

The initial selections preferably are performed with a large pool of candidate variant rRNAs. The pool of variant rRNAs can include at least $10^3$ molecules, e.g., at least $10^6$, $10^7$, $10^8$, $10^9$, $10^{11}$, $10^{12}$, or $10^{13}$ molecules. Variant rRNAs can be made with standard techniques including, for example, site-directed or preferably, random mutagenesis, of the gene encoding the rRNA, and in vitro transcription of the mutagenized gene to produce the variant rRNAs. See, Chapter 8 of *Short Protocols in Molecular Biology*, second edition, Ausubel et al., 1992, for a discussion of mutagenesis methods. Sequences of many prokaryotic 23S rRNAs (i.e., the major rRNA of the large ribosomal subunit in prokaryotes) are known. For example, sequences of 23S rRNA genes from *Escherichia coli* and *Bacillus stearothermophilus* have GenBank Accession Nos. J01695 g147581 and X01387 K02663, respectively. Brosius, J. et al., *Proc. Natl. Acad. Sci. USA*, 1980, 77:201–204; and Kopis et al., *DNA*, 1984 3(5):347–357. Sequences of eukaryotic 28S rRNAs (i.e, the major rRNA of the large ribosomal subunit in eukaryotes) also are known. For example, the 28S rRNA from *Xenopus laevis* has GenBank Accession No. X59734 g64487. See Ajun, P. M. et al., *Proc. R. Soc. Lond. B. Biol. Seq.*, 1991, 245(1312):65–71. The 28S rRNA gene from mouse has GenBank Accession No. X00525 g53988. See, Hassouna, N. et al., *Nucl. Acids Res.*, 1984, 12(8):3563–3588.

Specific point changes can be introduced into the gene encoding the rRNA molecule by oligonucleotide-directed mutagenesis. In this method, the desired change is incorporated into an oligonucleotide, which then is hybridized to the wild-type nucleic acid. The oligonucleotide is extended with a DNA polymerase, creating a heteroduplex that contains a mismatch at the introduced point change. The mismatch is repaired upon transformation of *E. coli*, and the gene encoding the variant rRNA can be re-isolated from *E. coli*. Kits for introducing site-directed mutations can be purchased commercially. For example, Muta-Gene® in-vitro mutagenesis kits can be purchased from Bio-Rad Laboratories, Inc. (Hercules, Calif.).

Random changes can be made by incubating a single-stranded DNA encoding an rRNA with chemicals that damage the base moiety of the nucleotide. For example, single-stranded DNA can be incubated with chemicals such as nitrous acid, formic acid, or hydrazine. After performing a primer extension, the DNA encoding the rRNA is isolated, used to transform *E. coli*, and mutagenized DNA then is recovered from *E. coli*.

Clusters of mutations can be introduced, for example, by using the linker scanning method. In this method, a plasmid encoding the rRNA is linearized near a region of interest, and digested with a nuclease such as Bal 31, or exonuclease III and S1 nuclease. Oligonucleotide linkers containing a restriction endonuclease site and mutated sequence then are ligated to the digested, plasmid ends. A complete plasmid is reconstructed by using the backbone from the wild type plasmid and the region of interest from the digested plasmid.

Polymerase chain reaction (PCR) techniques also can be used to introduce mutations. PCR is a procedure in which target nucleic acids are amplified. For random mutagenesis, degenerate oligonucleotides can be used to amplify the target nucleic acids. Alternatively, random mutagenesis can be performed under error-prone conditions including one or more of the following: increasing the concentration of magnesium chloride, adding manganese chloride, increasing and unbalancing concentrations of the four dNTPs, increasing the concentration of polymerase, or increasing extension time. See, Cadwell and Joyce, *PCR Methods and Applications*, 1992, 2:28–33. Point mutations also can be introduced by using oligonucleotides that incorporate the desired point change.

Variant rRNAs can be produced from the mutagenized DNA templates by in vitro transcription with T7 RNA polymerase under standard conditions. Other suitable RNA polymerases that can be used include, for example, SP6, T3, and *E. coli* RNA polymerases.

Preparation of Ribosomes

The methods described herein can be performed with eukaryotic or prokaryotic ribosomes. Intact ribosomes (70S for prokaryotic, 80S for eukaryotic) or the catalytically active large ribosomal subunits (50S for prokaryotes, 60S for eukaryotes) can be used. In either case, the large ribosomal subunit is reconstituted in vitro with a variant major rRNA (23S rRNA for prokaryotes or 28S rRNA for eukaryotes), wild-type minor RNAs (5S rRNA for prokaryotes, 7.8S and 5S for eukaryotes), and necessary ribosomal proteins. Functionally active 50S ribosomes from several organisms, including *Bacillus stearothermophilus*, *E. coli, Sulfolobus solfataricus*, and *Haloferax mediterranei*, have been reconstituted in vitro. Ribosomes from *B. stearothermophilus* are particularly amenable to reconstitution with in vitro transcripts while maintaining high activity. See, Green and Noller, *Biochemistry*, 1999, 38(6):1772–1779. One method for reconstituting includes isolating ribosomal proteins from rRNAs by extracting in acetic acid and dialyzing against an appropriate buffer or by extraction in urea/lithium chloride, followed by extraction with urea/magnesium treatment at pH 2.0. The 5S rRNA can be isolated by phenol extraction of associated proteins and ethanol precipitation or can be transcribed in vitro. Variant major rRNAs can be transcribed in vitro using standard procedures. The active subunit can be reconstituted by incubation of the purified proteins, purified minor rRNA(s), and the in vitro transcribed variant major RNA in a buffer containing monovalent and divalent cations for approximately 2 hours at 60° C. See, Green and Noller, *Biochemistry*, 1999, 38(6):1772–1779. Alternatively, the reconstitution can be performed in 4 mM magnesium for 20 minutes at approximately 40° C., followed by incubation in 20 mM magnesium for 90 minutes at 50° C. Reconstituted large subunits then can be combined with purified small subunits (30S for prokaryotic, 40S for eukaryotic) to produce intact 70S or 80S ribosomes.

Methods for Selecting rRNA Variants Catalyzing Formation of Non-peptidyl Products Substrates that crosslink to the peptidyl or aminoacyl site of ribosomes can be synthesized by standard methods. Photoaffinity crosslinking substrates are particularly useful. For example, s4TCPm can be prepared by standard phosphoramidite chemistry using a solid phase version of puromycin and rC and 4-thio-dT phosphoramidites. Aromatic ketone derivatized substrates, such as benzophenone-derivatized substrates can be prepared by the method of Kuechler et al., *Methods Enzymol.*, 1977, 46:676–683. A peptidyl or aminoacyl substrate can be crosslinked, for example, using ultraviolet (UV) light in the presence of reconstituted ribosomes and an appropriate mRNA template. Intact tRNAs (acylated or deacylated) can be added to increase the yield of the crosslink. For example, s4TCPm or benzophenone-derivatized peptidyl substrates (e.g., benzophenone derivatized Phe-tRNA$^{Phe}$ or Lys-tRNA$^{Lys}$) can be crosslinked to the A site or P site, respectively, of ribosomes by exposing to long wavelength UV light, e.g., 365 nm for about 10 minutes to about 2 hours.

After crosslinking a substrate to the A or P-site of the ribosome, the crosslinked ribosomes are reacted with a labeled, derivatized substrate under conditions that allow transfer of the labeled, derivatized substrate to variant rRNA molecules, i.e., conditions suitable for peptidyl transferase activity to occur. Suitable peptidyl transferase conditions include use of standard fragment or non-fragment reaction conditions. These conditions include a pH of 7.0 to 8.5, monovalent and divalent cations, and in the case of the fragment reaction, a primary alcohol. See, for example, U.S. Pat. No. 5,962,244 for a description of assay formats and conditions.

Selecting of Variant rRNAs

Labeled rRNAs are selected according to the label they carry. For example, if the derivatized substrate is labeled with biotin, streptavidin or avidin chromatography can be used to isolate labeled ribosomes, and in particular, labeled rRNAs. If the derivatized substrate is labeled by thiol derivatization, the variant rRNAs can be isolated by a thiol affinity column. See, for example, Lorsch and Szostak, *Nature*, 1994, 371:31–36. Selected rRNAs represent an enriched population of candidate molecules, and are amplified using standard procedures, including, for example, reverse-transcription to produce DNA templates, followed by PCR. The resulting PCR products are transcribed and passaged through another round of selection. The iterative process allows for isolation of rRNA variants that are highly enriched for particular catalytic properties demanded by the selection process. In vitro selection procedures have been used to identify molecules with catalytic functions. See, for example, Green et al., *Nature*, 1990, 347:406–408 and Lohse and Szostak, *Nature*, 1996, 381:442–4. For example, if the derivatized substrate is a D-amino acid, rRNA molecules are selected that, when incorporated into the large ribosomal subunit, have the ability to incorporate D-amino acids into a polymer. Typically, the complete cycle is repeated multiple times (i.e., crosslinking, reaction with labeled, derivatized substrate, and selection) using the same reagents. It is desirable to enrich the representation of the candidate variant rRNA by orders of magnitude. Selecting variant rRNAs with particular catalytic properties allows the function of the ribosome to be evolved. Coupling of the evolved ribosome with RNA peptide fusion technology (Robert and Szostak, *Proc Natl Acad Sci USA*, 1997, 94(23):12297–302) is a powerful tool for deconvolution of complex combinatorial libraries.

The invention will be further described in the following examples, which do not limit the scope of the invention described in the claims.

EXAMPLES

Example 1

Materials and Methods

Synthesis of 4-thio-dT-p-C-p-puromycin 5'-Dimethoxytrityl-Nα-trifluoroacetyl-puromycin was attached to alkylamine-derivatized controlled pore glass via a 2'-succinate linkage by standard methods. See, Atkinson and Smith, Solid Phase Synthesis of Oligodeoxyribonucleotides by the Phosphate-triester Method, in *Oligonucleotide Synthesis: A Practical Approach*, Oxford: IRL Press, pp. 35–81, 1985. 4-Thio-dT-p-C-p-Puromycin (s$^4$TCPm) was prepared by standard phosphoramidite chemistry using the solid-phase version of puromycin, and rC and 4-thio-dT phosphoramidites (Glen Research Corporation, Sterling, Va.). Deprotection was performed by treatment with 3:1 NH$_4$OH:MeOH/50 mM NaSH overnight at 55° C. Subsequently, 40 equivalents of 1 M tetrabutylammonium fluoride (TBAF) in tetrahydrofuran (THF) were added to the dried product and incubated overnight at room temperature. Finally, 20 mM triethylamine-acetate (pH. 7.0) was added to the reaction mixture, loaded directly on a C18 HPLC column, and eluted with increasing concentrations of acetonitrile (CH$_3$CN). Multiple peaks were collected and the purity of the products was analyzed on a 20% polyacrylamide/7M urea gel following 5'-[$^{32}$P]-end-labelling using polynucleotide kinase. Although two peaks appeared to be relatively pure by this analysis, only the slowest migrating peak on the HPLC had any crosslinking ability. Kinetic characterization of s$^4$TCPm was performed using the tRNA fragment N-Ac-Met-ACCACC, as a P-site substrate, using fragment reaction conditions, and paper electrophoresis analysis of the resulting product, s$^4$TCPm-N-Ac-Met, as described by Green and Noller, *RNA*, 1996, 2:1011–1021. This analysis was complicated by the apparent affinity of the compound for both the A and P sites at high concentrations. The P-site affinity may be attributable to wobble pairing between 4-thio-dT (which mimics C74 of tRNA) and G2252 of 23S rRNA. See, Samaha et al., *Nature* 1995, 377:309–314.

Isolation of 70S Tight Couple Ribosomes: Wild-type (pLK45(PSI/PSII)) and mutant *E. coli* 70S tight-couple ribosomes were isolated from wild-type (pLK45(PSIles II) *E. coli*, mutant *E. coli* and *B. stearothermophilus* as described by Powers and Noller, *EMBO J.*, 1991, 10:2203–2214. In general, bacterial cultures were pelleted and washed in buffer containing 50 mM Tris-HCl, pH 7.6, 10 mM MgCl$_2$, 100 mM NH$_4$Cl, 6 mM 2-mercaptoethanol, and 0.5 mM EDTA. Cells were lysed by two consecutive passes through a French press at 18,000 p.s.i, then treated with DNase I, and centrifuged twice for 15 minutes at 15000 rpm in a Sorvall SS34 rotor at 4° C. After adjusting the NH$_4$Cl concentration to 0.5M, ribosomes were pelleted for 4 hours at 40,000 rpm in a Ti-60 rotor at 4° C. The crude ribosome pellet was washed in 50 mM Tris-HCl, pH 7.6, 6 mM MgCl$_2$, 100 mM NH$_4$Cl, and 6 mM 2-mercaptoethanol, and loaded onto a 10–40% sucrose gradient in the same buffer. Fractions containing the 70S ribosomes were collected, and the MgCl$_2$ concentration was raised to 10 mM. Ribosomes were pelleted for 13 hours at 40,000 rpm in a Ti-60 rotor at 4° C., and washed and resuspended in the same buffer.

Crosslinking of ribosomes by s$^4$TCPm: Tight-couple *E. coli* 70S ribosomes (2 μM) were incubated with 1.2 equivalents (2.4 μM) of gene 32 mRNA and of deacylated CF23 tRNA$^{Phe}$ in 20 mM Tris, pH 7.5, 30 mM MgCl$_2$, 50 mM NH$_4$Cl, 6 mM 2-mercaptoethanol, and 10% MeOH. Saturating s$^4$TCPm (20 μM) (or [$^{32}$P]-s$^4$TCPm) was then added and the mixture was incubated at 37° C. for 10 minutes. Crosslinking of s$^4$TCPm to *B. stearothermophilus* 70S ribosomes was performed under similar conditions except with 30 mM Tris pH 7.5, 10 mM MgCl$_2$, and 330 mM KCl. Complexes were exposed for varying lengths of time to a hand-held UV light source (UVL-56, Blak-Ray Lamp, UVP, Inc.—366 nm) at a distance of 3 cm. Intact rRNAs were phenol extracted, and resolved on 3.8% polyacrylamide/7 M urea gels. Quantification of the radioactivity attached to 23S rRNA indicates that at least 30% of the ribosomes can be derivatized with s$^4$TCPm. Analysis of the amount of substrate crosslinked to the r-proteins was determined as described by Breitmeyer and Noller, *J. Mol. Biol.*, 1976, 101:297–306.

Crosslinking was performed of 70S tight-couple ribosomes (20 pmol) also using 300 pmol of s$^4$TCPm in a total volume of 15 μl. The resulting mixture was incubated at 37° C. for 10 minutes and exposed to UV light for 15 minutes. The rRNAs were subsequently isolated and allele-specific primer extension (using PSII) was performed as described by Samaha et al., *Nature*, 1995. 377:309–314.

Construction and analysis of tRNA$^{Phe}$ mutants: Templates for transcription of mutant tRNA$^{Phe}$ were generated by PCR amplification of CF23 plasmid using the following primers: T7 top, 5'-TAA-TAC-GAC-TCA-CTA-TAG-3'; ΔA, 5'-GGT-GCC-CGG-ACT-CGG-AAT-CGA-3'; ΔCA, 5'-GTG-CCC-GGA-CTC-GGA-ATC-GAA-3'; C74A, 5'-TGT-TGC-CCG-GAC-TCG-GAA-TCG-3'; C75A, 5'-TTG-TGC-CCG-GAC-TCG-GAA-TCG-3'; and A76C, 5'-GGG-TGC-CCG-GAC-TCG-GAA-TCG-5'. Amplified DNA was extracted once with phenol and once with chloroform, precipitated with ethanol, and transcribed in vitro with T7 polymerase under conditions described by Milligan et al., *Nucl. Acids Res.*, 1987, 15:8783–8798, with the following alterations: 2 mM each NTP, 10 mM GMP, and 14 mM MgCl$_2$ were used. Crude transcription reactions were purified on 55 cm long, 1 mm thick, 7 M urea/12% acrylamide gels with the xylene cyanol dye marker run to the bottom. Transcripts were passively eluted into 0.3 M sodium acetate (NaOAc), extracted with phenol and chloroform, and precipitated. RNAs then were labeled with [$^{32}$P]-Cp and T4 RNA ligase, and digested to completion with 1 unit of RNase T2 in 100 mM NH$_4$OAc, pH 5.4 at 37° C. for 120 minutes. Np (Ap, Cp, Gp, and Up) products were resolved by paper electrophoresis at pH 3.5 (pyridine-acetate) (30 minutes at 3000 V).

Mapping of crosslinked site in 23S rRNA: Radioactively labeled crosslinked 23S rRNA species were digested with RNase T1 in 0.2 M NaOAc, pH 5.5, 2.5 mM EDTA at 37° C. for 20 minutes and the products were resolved on 24% polyacrylamide/6 M urea gels. RNase H digestion analysis was performed using the following oligonucleotides: 5'-TGA-TGT-CCG-ACC-AGG-ATT-AG-3' (nt 2295-2314 of 23S rRNA); 5'-GAC-CTA-CTT-CAG-CCC-3' (nt 2523-2538 of 23S rRNA); and 5'-ACC-GAA-CTG-TCT-CAC-GA-3' (nt 2593-2609 of 23S rRNA). Primer extension analysis was performed on ribosomal complexes formed in the presence or absence of unlabeled s$^4$TCPm compound using an oligonucleotide having the sequence 5'-ACT-AGG-AGC-AGC-CCC-CC-3' (nt 2639 of 23S rRNA).

23S rRNA mutant construction and growth phenotypes: Oligonucleotide directed mutations were constructed in pBS23S using mutagenic primers 2552(A/C/G), 5'-CAA-GGG-TAT-GGC-(A/C/G)GT-TCG-CCA-TTT-AA-3', and 2553(A/C/U), 5'-CAA-GGG-TAT-GGC-T(A/C/U)T-TCG-CCA-TTT-AA-3'. Expression plasmids were constructed by digestion of mutant derivatives of pBS23S with Asp718 and ligation to BamH1 linkers. The resulting linear plasmid was digested with BamH1 and Sph1 and introduced into plasmid pLK45(PSI/PSII) containing the rrnB operon under control of phage lambda PL promoter. See, Powers and Noller, *Proc. Natl. Acad. Sci. USA*, 1990, 87:1042–1046. Mutant plasmids were transformed into *E. coli* strain DH1 containing the plasmid pcI857, which encodes a thermolabile allele of the lambda repressor. The resulting pLK plasmids contain the engineered priming sites PSI and PSII, the A2058G erythromycin resistance marker, and the respective mutations. Cells were selected on plates containing ampicillin (100 mg/l) and kanamycin (40 mg/l), and on plates containing ampicillin (100 mg/l), kanamycin (40 mg/l), and erythromycin (200 mg/l) at 30° C. (uninduced) or 42° C. (induced) for the analysis of dominant and recessive phenotypes.

Kinetic analysis of crosslinked ribosomal complex: Crosslinked 50S subunits were separated from 30S subunits, gene 32 mRNA, and deacylated tRNA$^{Phe}$ on 5%–20% sucrose gradients in 10 mM Tris-Cl, pH 7.5, 30 mM NH$_4$Cl, and 1 mM MgCl$_2$, and spun in an SW41 rotor at 19,000 rpm for 16 hours. Excess sucrose was removed and the buffer exchanged to 20 mM Tris, pH 7.5, 100 mM NH$_4$Cl, and 5 mM MgCl$_2$ using Centricon 100 tubes spun at 2600 rpm in an SS34 rotor. Peptidyl transferase assays were done as follows: crosslinked 50S subunit complexes (0.5 µM) were incubated in standard fragment reaction conditions (50 mM Tris, pH 8.3, 0.4 M potassium acetate (KOAc), 60 mM MgCl$_2$, and 33% MeOH) with CACCA-(N-Ac-Phe) (2 µM). Aliquots were removed from the reaction at the indicated times, rRNAs phenol extracted, digested with RNase T1, and the fragments resolved on 24% polyacrylamide/6 M urea gels. For inhibition analysis, antibiotics were added to the reaction mixture described above at the following concentrations: chloramphenicol (0.1 mM), carbomycin (0.1 mM), clindamycin (0.1 mM), erythromycin (0.1 mM), neomycin (0.01 mM), sparsomycin (0.1 mM) and puromycin (1 mM). When incubated with ribosomes at these concentrations, these antibiotics protect specific positions in 16S and 23S rRNA from chemical modification. Antibiotic inhibition of crosslinking was performed using limiting [$^{32}$P]-s$^4$TCPm and a single time point (2 minutes) of exposure to various lengths of time (0, 5, 10, 20, or 40 minutes) to long-wave length (366 nm) UV light (in the linear range of the reaction) under standard conditions. Ribosomal RNAs were phenol extracted and analyzed on a 3.8% polyacrylamide—7 M urea gel. Antibiotic inhibition of PT activity was performed with the fragment P-site substrate, CACCA-(N-Ac-Phe), supplied at a concentration of 0.3 µM; a single linear time point of 4 minutes was used for analysis.

Example 2

Figure 3A:
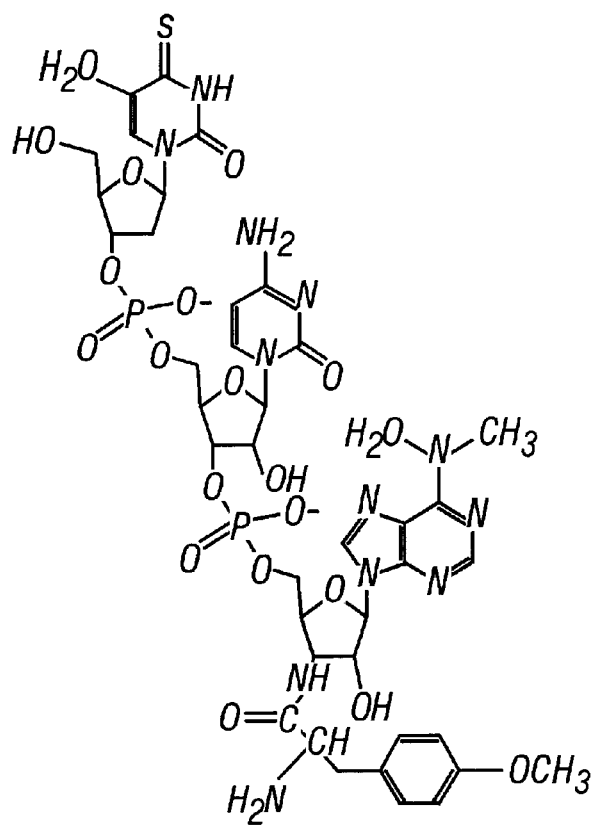
FIG. 3A is the chemical structure of $s^4$TCPm. The sulfur (on 4 thio-dT) required for the crosslinking chemistry and the primary amine (on puromycin) involved in peptidyl transferase chemistry are shaded.

Synthesis of an A-site specific crosslinking reagent: The antibiotic puromycin is an aminoacyl-tRNA analogue that functions as an A-site substrate of peptidyl transferase and terminates protein synthesis as a consequence of the stable amide linkage joining its aminoacyl and ribose moieties. This compound is of potential interest for a variety of applications where its properties can be exploited to form a stable link between protein and nucleic acid, and consequently, between phenotype and genotype. Puromycin was immobilized on a solid-phase support for incorporation into oligonucleotides using standard phosphoramidite chemistry as described in Example 1. Synthesis and characterization of C-p-Puromycin (CPm) by mass spectrometry confirmed the identity of the immobilized reagent. Kinetic experiments show that the affinity of CPm for the peptidyl transferase A site is greater than that of puromycin by more than an order of magnitude; the Km of puromycin is ca. 400 µM, whereas the Km of CPm is ca. 10 µM. These data are consistent with experiments suggesting that important contacts are made by the ribosome with the C75 position of A-site bound tRNAs. Next, the compound 4-thio-dT-p-C-p-Puromycin (s$^4$TCPm) was chemically synthesized and purified on a reverse-phase (C18) HPLC column (FIG. 3A). The Km of this compound for the A site of the 50S subunit is similar to that of CPm, ca. 10 µM.

Example 3

Figure 3B:
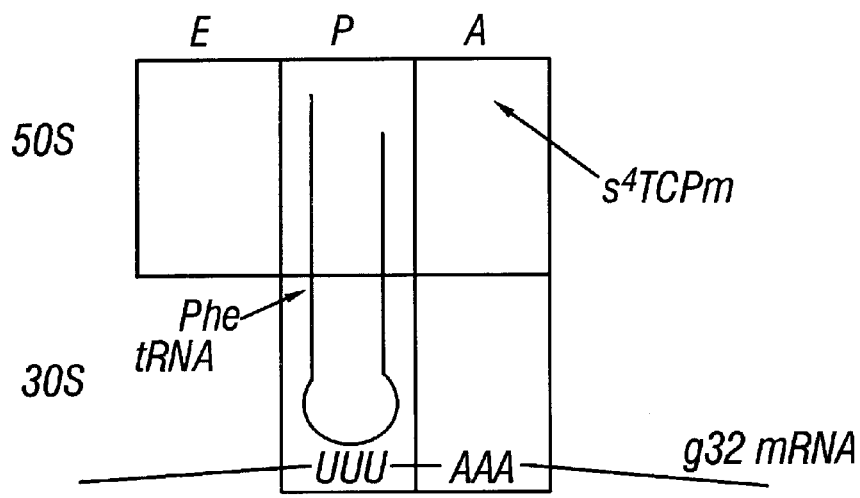
FIG. 3B is a schematic of ribosomal complex formed with tight-couple 70S ribosomes, gene 32 mRNA, and deacylated tRNA$^{Phe}$ to direct binding of s$^4$TCPm specifically to the large subunit A site.

Crosslinking to the peptidyl transferase A site: To target binding of the crosslinking reagent specifically to the peptidyl transferase A site, the P site of *E. coli* tight-couple 70S ribosomes, programmed with a shortened version of bacteriophage T$_4$ gene 32 mRNA, was filled with deacylated tRNA$^{Phe}$, followed by binding of radioactively labeled [$^{32}$P]-s$^4$TCPm (FIG. 3B). The complex was exposed for increasing lengths of time to long wave-length (366 nm) UV light. Total RNA was prepared from the UV-irradiated ribosomal complexes by phenol extraction and analyzed on a 3.8% denaturing polyacrylamide gel. Covalent labeling of 23S rRNA, and not 16S or 5S rRNA, was consistent with crosslinkling to the peptidyl transferase center of the ribosome, which is located on the 50S subunit. The crosslinking reaction was complete after 10 minutes of UV irradiation. Based on [$^{32}$P] incorporation into 23S rRNA, it was estimated that 30% of ribosomes were crosslinked in the presence of 20 µM s$^4$TCPm. The absence of significant crosslinking to ribosomal proteins provides support for the RNA-rich environment of the peptidyl transferase site and for the specificity of the crosslinked A-site ribosomal complex. More specifically, these data indicate that the A site of the 50S subunit was composed, at least partially, of 23S rRNA.

Figure 4:
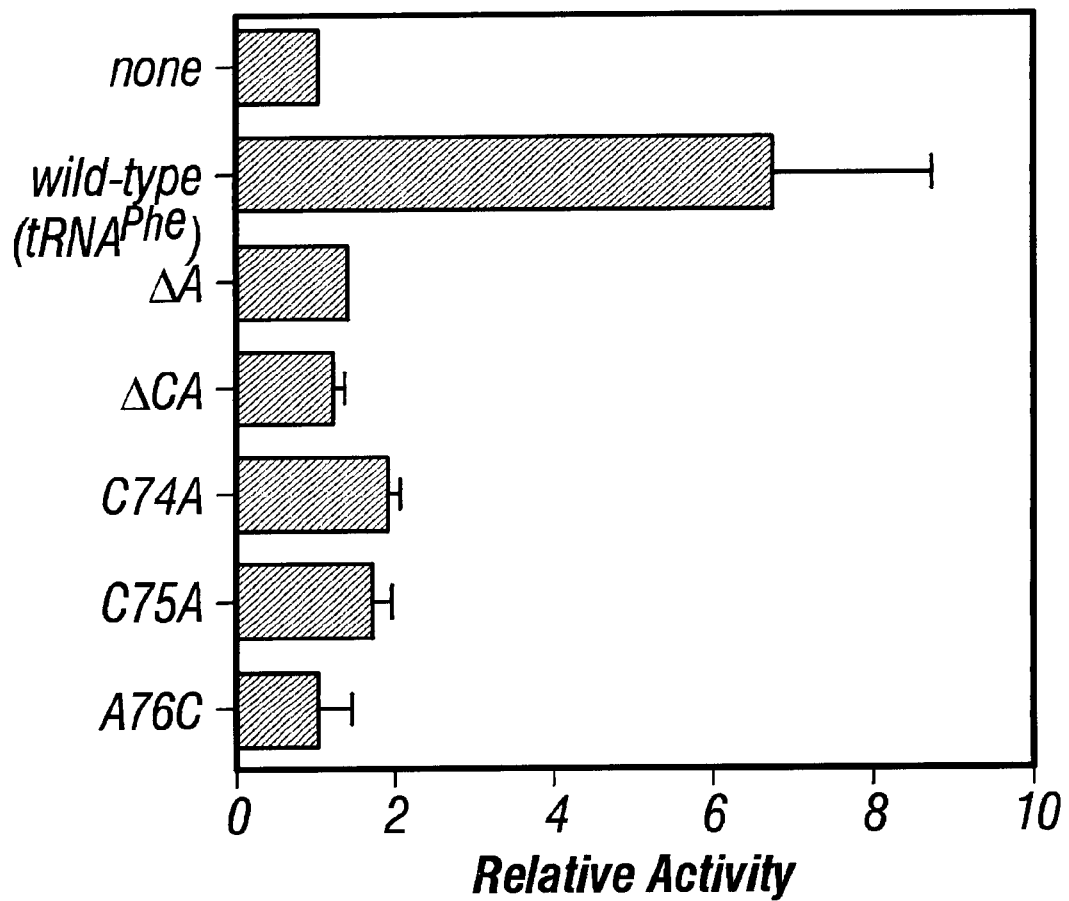
FIG. 4 is a graph that indicates relative activity of tRNA$^{Phe}$ species with mutant CCA acceptor ends. Ribosomal complexes were formed as described in FIG. 3B with the indicated alterations of the CCA acceptor end of deacylated tRNA$^{Phe}$ in the P site and limiting [$^{32}$P]-s$^4$TCPm in the A site and exposed to UV light. Radioactivity incorporated into 23S rRNA was normalized to the amount incorporated in the absence of any tRNA$^{Phe}$.

Intriguingly, crosslinking of s$^4$TCPm was strongly dependent on occupancy of the P site with deacylated tRNA$^{Phe}$ (FIG. 4). To ask which particular features of P-site tRNA were required for binding to the A site, several mutant versions of tRNA$^{Phe}$ were constructed, containing deletions (ΔA76 and ΔCA76) and point mutations (C74A, C75A and A76C) in its CCA terminus. The integrity of the 3' termini of the mutant tRNAs (at least 75% correct) was confirmed by end-labeling with [$^{32}$P]-pCp and RNA ligase, digestion to completion with RNase T2, and analysis of the mononucleotide products by paper electrophoresis. The altered tRNAs, when bound to the P site, were not able to support efficient crosslinking of s$^4$TCPm in the A site; crosslinking levels were reduced nearly to the background level observed in the absence of any P-site bound tRNA (FIG. 4). Consistent with a specific Watson-Crick interaction in the P site between C74 of tRNA and G2252 of 23S rRNA, the inability of C74A mutant tRNA to stimulate efficient A site s$^4$TCPm crosslinking was suppressed in the context of G2252U mutant ribosomes. Thus, a properly engaged, intact P-site bound tRNA was required for formation of this highly efficient A-site crosslink. These results were most simply explained by the hypothesis that the A site on the 50S subunit was incompletely formed (or was inaccessible) in the absence of P-site-bound tRNA. It can be inferred that either the 50S subunit undergoes a conformational change as a result of P-site tRNA binding, thus creating (or revealing) the A site, or that the P-site tRNA itself provides one or more of the A-site binding determinants.

Example 4

Characterization of the crosslinked 23S rRNA species: The complexity of the crosslinked E. coli 23S rRNA species was characterized by complete digestion with RNase T1. Analysis of the resulting oligonucleotide fragments on a 6 M urea/24% acrylamide gel revealed a single crosslinked product that migrated more slowly than the [$^{32}$P]-labelled substrate; given the resolving power of such a high percentage gel, it seems likely that a single crosslinked 23S rRNA species was formed. The efficiency and specificity of crosslinking of s$^4$TCPm to its rRNA target is reminiscent of that between position 34 of certain tRNAs and position C1400 of 16S rRNA. Typically, highly efficient crosslinks to the ribosome, such as those obtained with benzophenone-derivatized Phe-tRNA$^{Phe}$, target multiple rRNA sites.

The position of the crosslinked A-site substrate was first localized with a series of RNase H digestions to the region between positions 2538 and 2593 of 23S rRNA. Assignment of the site of crosslinking to position G2553 was achieved using primer extension analysis. Because of the impaired ability of reverse transcriptase to read modified bases on the rRNA template, a major cDNA product was obtained terminating one nucleotide 3' to the modified base. The strong stop induced by crosslinking with s$^4$TCPm was consistent with the estimated crosslinking efficiency of 30%. The spontaneous stop observed in all lanes at Um2552 results from a post-transcriptional 2'-O-methyl modification. Some "stuttering" by reverse transcriptase is seen, corresponding to stops±one nucleotide from the principle band; this is commonly observed, and believed to result from premature termination due to steric interference on the 3' side, or limited read-through at the modified position. Parallel crosslinking experiments with s$^4$TCPm and B. stearothermophilus ribosomes indicated that crosslinking was similarly efficient and also yielded a single RNase T1 product. Primer extension analysis of B. stearothermophilus 23S rRNA again identified the crosslinked position to be nucleotide G2553 (E. coli numbering). The reduced mobility of the RNase T1 product from the crosslinked rRNA was consistent with covalent attachment of a small oligonucleotide (3 nucleotides) to s$^4$TCPm, suggesting that RNase T1 was able to cleave the phosphodiester backbone following the crosslinked G2553 under the conditions used.

The high specificity and efficiency of the crosslink between the minimal A-site substrate, s$^4$TCPm, and 23S rRNA identifies the 2555 loop as a site of interaction with the conserved CCA end of A-site tRNA. G2553 is one of seven nucleotides protected from chemical modification by intact tRNA bound in the A site of the 50S subunit; indeed, it was the only base whose protection correlates precisely with the presence of the terminal adenosine (A76) of tRNA. Moreover, the antibiotic puromycin weakly footprints G2553 and an electrophilic derivative of puromycin weakly crosslinks to an oligonucleotide sequence in 23S rRNA consistent with the labeling of U2555. Interestingly, the peptidyl transferase transition state analogue, the phosphoramidate of CCdAp and puromycin (CCdApPuro), yielded a characteristic P-site carbodiimide chemical footprint at U2585, but no corresponding A-site footprint at U2555 or U2609, suggesting that in this background, the contacts of puromycin to the ribosome are dominated by the stronger P-site interactions (e.g. between G2252 of 23S rRNA and C74 of tRNA). Cleavage of the RNA backbone on the 3' side of the 2555 loop and stem by hydroxyl radicals generated from Fe(II) tethered to the 5' end of tRNA bound to the A site is also consistent with its proximity to the peptidyl transferase A site. Sequence conservation in the 2555 loop of 23S rRNA is extreme; both G2553 and its neighbor, Um2552, are universally conserved nucleotides, suggesting the possibility of direct Watson-Crick, or other, pairing interactions between this feature of 23S rRNA and the similarly conserved CCA end of A-site bound tRNA.

Example 5

Site-directed mutations in the 2555 loop of 23S rRNA: Because of the extreme sequence conservation of the 2555 loop of 23S rRNA, site-directed mutations were introduced at positions Um2552 (A, C, and G) and G2553 (A, C, and U) to test their effects on cellular growth and the ability of mutant ribosomes to support the A-site crosslinking reaction. The mutant 23S rRNA was expressed as part of an rrnB operon-containing plasmid construct under transcriptional control of the inducible lambda PL promoter by induction at 42° C., producing cells that contain a mixture (ca. 50/50) of mutant and chromosomally-encoded wild-type ribosomes. Under these conditions, dominant growth phenotypes can be observed. The mutant 23S rRNA also carries an erythromycin resistance mutation (A2058G), allowing recessive phenotypes to be observed. Under erythromycin selection, cell growth is dependent on the plasmid-encoded 23S rRNA. None of the mutations at Um2552 conferred dominant phenotypes; all exhibited severe recessive growth deficiencies when grown in the presence of erythromycin (Table 1). These in vivo phenotypes are consistent with those reported earlier for Um2552 A and Um2552 C by Porse and Garrett, i J. Mol. Biol., 1995, 249:1–10; these authors also reported mild peptidyl transferase defects to be associated with these mutations. By contrast, all mutations at G2553 conferred a dominant growth defect; the phenotype of G2553 C was less severe than G2553 A or G2553 U. All mutations at G2553 had severe growth defects when grown in the presence of erythromycin (Table 1). Wild-type 23S rRNA, pLK45(PSI/PSII), carries two allele-specific priming sites and the erythromycin resistance mutation, A2058G; mutant 23S rRNAs were expressed in this same background. In Table 1, growth similar to that of the wild-type strain, as assessed by colony size, is indicated as "++", slow growth is indicated as "+", and no visible growth is indicated as "−".

TABLE 1

Growth phenotypes of cells expressing 23S rRNA mutations at positions Um2552 and G2553

|  | $Amp_{100} Kan_{40}$ | | $Amp_{100} Kan_{40} Ery_{200}$ | |
| --- | --- | --- | --- | --- |
|  | 30° C. | 42° C. | 30° C. | 42° C. |
| pLK45(PSI/PSII) | ++ | ++ | ++ | ++ |
| Um2552A | ++ | ++ | ++ | − |
| Um2552C | ++ | ++ | ++ | − |
| Um2552G | ++ | ++ | ++ | − |
| G2553A | ++ | − | ++ | − |
| G2553C | ++ | + | ++ | − |
| G2553U | ++ | − | ++ | − |

The effects of Um2552 and G2553 mutations on the efficiency of crosslinking $s^4$TCPm to the 23S rRNA A-site was examined. The extent of crosslinking in the mutant ribosome population can be followed by primer extension analysis, taking advantage of silent mutations incorporated into the cloned copy of 23S rRNA, which allow for allele-specific primer extension. Consistent with the observed in vivo phenotypes, all three mutations at G2553 abolish crosslinking of $s^4$TCPm. In contrast, at least one mutation, Um2552G, supports efficient crosslinking. The severe phenotypes resulting from single nucleotide changes in 23S rRNA at position G2553 were consistent with involvement of this region of the molecule in functionally important interactions with the A-site substrate. Neighboring mutations at U2555 (to A and G) have been identified as suppressors of −1 frameshifting, similarly implicating this region of 23S rRNA in A-site interactions critical to the fidelity of translation.

Example 6

Peptidyl transferase reactivity of the crosslinked complex: Crosslinked E. coli 50S subunit-$s^4$TCPm complexes were separated from 30S subunits, deacylated tRNA$^{Phe}$, and gene 32 mRNA, by sucrose gradient sedimentation and tested for the ability of the covalently bound A-site substrate to participate in peptide bond formation. The minimal P-site oligonucleotide substrate CACCA-(N-Ac-Phe) was supplied under fragment reaction conditions and its reaction with the crosslinked puromycin complex was followed by a shift in the electrophoretic mobility of the RNase T1 fragment resulting from acquisition of N-Ac-Phe. After a reaction time of 2 minutes, approximately 50% of the crosslinked population reacted with the P-site substrate, and by 12 minutes, the reaction was substantially complete (85%). The rate of reaction of the covalently bound substrate was similar to that observed in a standard fragment reaction with 50S subunits in which free puromycin was supplied at a saturating concentration. Crosslinked B. stearothermophilus 50S-$s^4$TCPm complexes were similarly reactive with minimal P-site substrates in a peptidyl transferase reaction, though the kinetics for the thermophilic ribosomes were considerably slower (ca. 10-fold). These data indicate that the A-site substrate was crosslinked to 23S rRNA in its biologically active configuration.

The displacement and hybrid state models for the movements of tRNA substrates in the translational elongation cycle both invoke coupling of the peptidyl transferase reaction with movement of the acceptor end of A-site-bound tRNA into the P site of the 50S subunit. Because the A-site substrate in the crosslinked complex was covalently tethered, substantial movement was hindered. The efficient catalysis performed by the crosslinked complex suggests that either the crosslinked product retains sufficient mobility to undergo movement (which may be modest), that movement was coupled to intramolecular rearrangement of 23S rRNA, or that peptidyl transfer and movement are sequential, rather than concerted.

Example 7

Figure 5B:
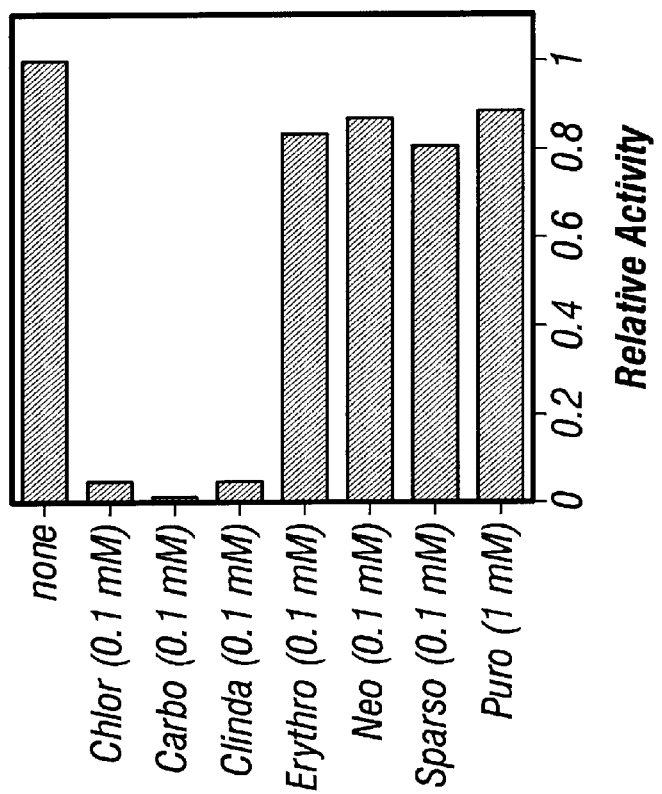
FIGS. 5A and 5B are graphs that indicate antibiotic inhibition of crosslinking by s$^4$TCPm to 23S rRNA (5A) and of peptidyl transferase activity of crosslinked complex (s$^4$TCPm-50S) (5B). Values were normalized to 1.0 for reactions where no antibiotics were included.
Figure 5A:
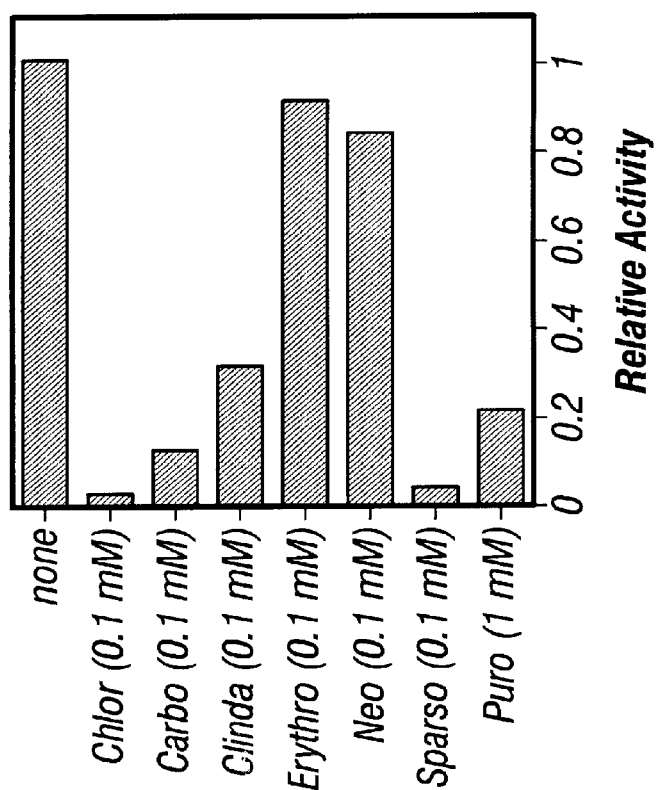

Antibiotic inhibition of crosslinking and PT activity: A number of peptidyl transferase-specific antibiotics, including chloramphenicol, carbomycin, clindamycin, sparsomycin, and puromycin specifically inhibited the crosslinking of $s^4$TCPm to the 2555 loop of 23S rRNA. In contrast, erythromycin, a 50S subunit-specific antibiotic that does not directly affect peptidyl transferase, and neomycin, a 30S subunit-specific antibiotic, had no effect (FIG. 5A). Of this same group of antibiotics, only chloramphenicol, carbomycin, and clindamycin effectively inhibited the peptidyl transferase reactivity of the crosslinked complex (FIG. 5B). Interestingly, sparsomycin, a peptidyl transferase-specific antibiotic, strongly inhibited the crosslinking reaction, but had no inhibitory effect on the reactivity of the crosslinked complex. While sparsomycin is known to stabilize P-site substrate binding, it also competes effectively for binding with puromycin in the A site. As sparsomycin is ineffective in the context of a covalently tethered puromycin substrate, but active in preventing the crosslinking of $s^4$TCPm, it seems likely that its mode of inhibition results primarily from its effect on A-site interactions. Puromycin had no effect on the peptidyl transferase activity of the crosslinked complex, consistent with the high effective concentration of the $s^4$TCPm substrate covalently bound in the A site. These effects of the various antibiotics on the activity of the 50S subunit-$s^4$TCPm complex provide further evidence that the synthetic substrate, $s^4$TCPm, is crosslinked to its physiologically correct binding site.

Figure 6:
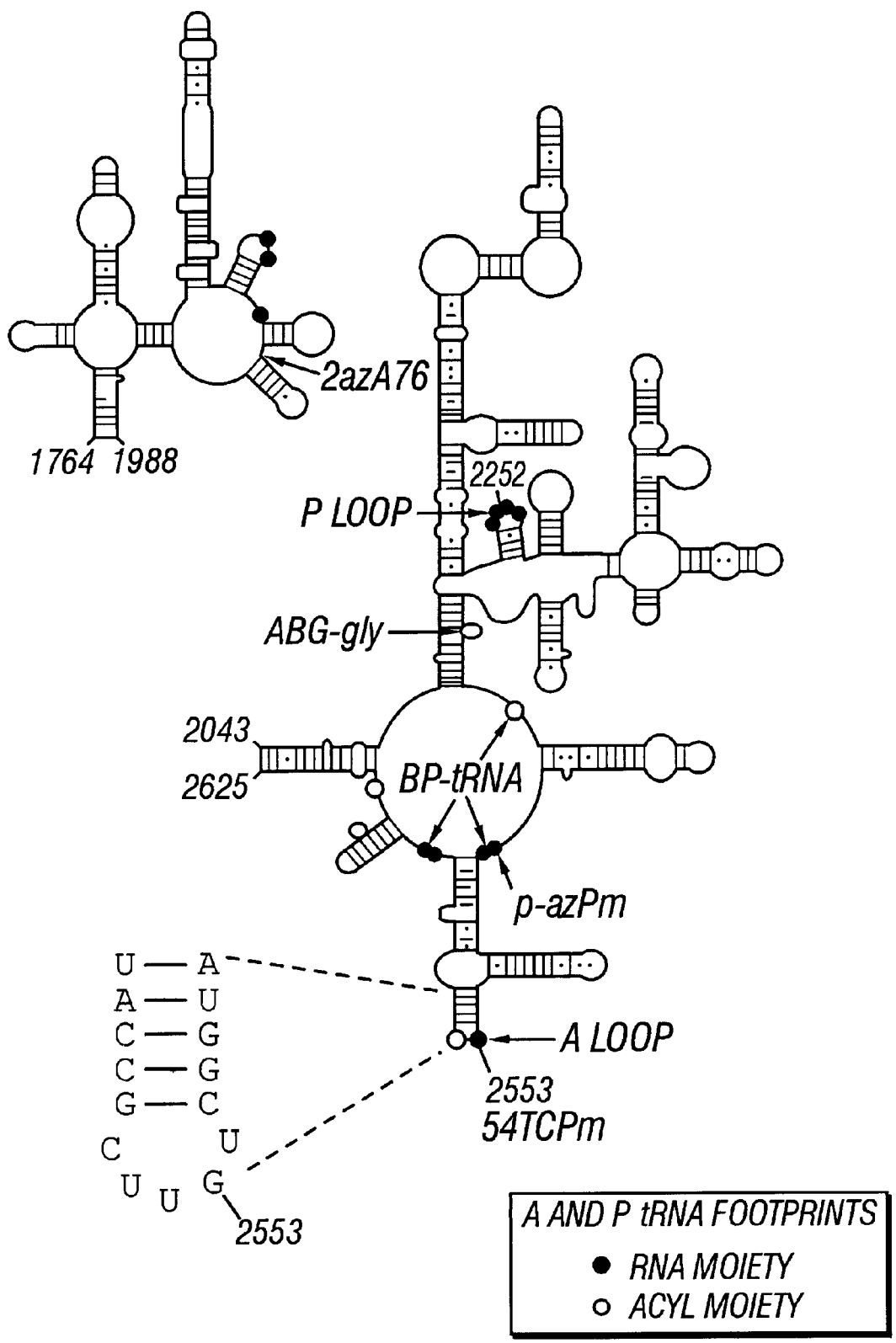
FIG. 6 is the secondary structure of domains IV (part) and V of 23S rRNA. The footprints of A and P site tRNAs (closed circles for RNA protected moieties and open circles for acyl protected moieties) are indicated. Several sites crosslinked by the acceptor end of P- and A-site-bound tRNAs are indicated with small arrows; 2azidoA76, ABG-gly, p-azidoPm, and benzophenone-tRNA. Two specific nucleotides, G2252 and G2553, known to form close contact with the CCA end of P- and A-site-bound tRNAs, respectively, are indicated; the loops in which these nucleotides are found are designated the P loop and the A loop. The sequence of the 2555 loop is shown in the inset; the universally conserved nucleotides are indicated by boldface lettering.

Localization of the 2555 loop of 23S rRNA to the peptidyl transferase A site expands the understanding of the nature of the elusive peptidyl transferase center of the ribosome (FIG. 6). Taken together with previous genetic data identifying the 2250 loop (or P loop) of 23S rRNA as a binding determinant for the CCA-end of P-site bound tRNA and a peptidyl transferase-reactive crosslink to A2451/C2452 in the central loop of domain V, it becomes clear that the "active site" is composed of a number of distal elements dispersed across the secondary structure of domain V of 23S rRNA.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for selecting rRNA variant molecules catalyzing formation of non-peptidyl products, the method comprising:

a) crosslinking a peptidyl substrate to ribosomes, wherein the major RNA of the large ribosomal subunit in a plurality of the ribosomes is an rRNA variant molecule;

b) reacting the crosslinked ribosomes and a labeled, derivatized aminoacyl substrate under conditions such that the labeled, derivatized aminoacyl substrate is transferred to the rRNA variant molecule to form labeled ribosomes; and c) selecting the rRNA variant molecules from labeled ribosomes.

2. The method of claim 1, wherein the method further comprises repeating steps a)–c) with said selected rRNA variant molecules.

3. The method of claim 1, wherein the peptidyl substrate is a benzophenone derivatized peptidyl substrate.

4. The method of claim 1, wherein the labeled, derivatized aminoacyl substrate is N-derivatized.

5. The method of claim 1, wherein the labeled, derivatized aminoacyl substrate comprises a β-amino acid.

6. The method of claim 1, wherein the labeled, derivatized aminoacyl substrate comprises a D-amino acid.

7. The method of claim 1, wherein the labeled, derivatized aminoacyl substrate is biotinylated.

8. The method of claim 1, wherein the labeled aminoacyl substrate comprises a thiol moiety.

9. The method of claim 1, wherein the rRNA variant is a 23S rRNA variant molecule.

10. The method of claim 1, wherein the rRNA variant is a 28S rRNA variant molecule.

11. The method of claim 1, wherein the ribosomes are eukaryotic.

12. The method of claim 1, wherein the ribosomes are prokaryotic.

13. The method of claim 12, wherein the prokaryotic ribosomes are *Escherichia coli* ribosomes.

14. The method of claim 12, wherein the prokaryotic ribosomes are *Bacillus stearothermophilus* ribosomes.

15. A method for selecting rRNA variant molecules catalyzing formation of non-peptidyl products, the method comprising:

a) crosslinking an aminoacyl substrate to ribosomes, wherein the major RNA of the large ribosomal subunit in a plurality of the ribosomes is an rRNA variant molecule;

b) reacting the crosslinked ribosomes and a labeled, derivatized peptidyl substrate under conditions such that the labeled, derivatized peptidyl substrate is transferred to the rRNA variant molecule to form labeled ribosomes; and c) selecting the rRNA variant molecules from the labeled ribosomes.

16. The method of claim 15, wherein said method further comprises repeating steps a)–c) with said selected rRNA variant molecules.

17. The method of claim 15, wherein the aminoacyl substrate is 4-thio-dT-p-C-p-Puromycin.

18. The method of claim 15, wherein the labeled, derivatized peptidyl substrate comprises a methyl phosphinyl derivatized peptidyl substrate.

19. The method of claim 15, wherein the labeled, derivatized peptidyl substrate comprises a D-amino acid.

* * * * *